United States Patent

Forbes

Patent Number: 5,671,699
Date of Patent: Sep. 30, 1997

[54] TORSO-SETTLING HARNESS FOR TRUCK DRIVERS

[76] Inventor: Daniel A. Forbes, 3911 NW. 165th St., Opa Locka, Fla. 33050

[21] Appl. No.: 674,162

[22] Filed: Jul. 1, 1996

[51] Int. Cl.⁶ .................................................. A62B 35/06
[52] U.S. Cl. .......................................................... 119/857
[58] Field of Search .................................... 119/850, 856, 119/857, 907; 128/874, 875

[56] References Cited

U.S. PATENT DOCUMENTS

| | | | |
|---|---|---|---|
| 3,780,663 | 12/1973 | Pettit | 119/857 X |
| 4,273,215 | 6/1981 | Leggett | 119/857 X |
| 4,324,205 | 4/1982 | Goldmacher | 119/96 |
| 4,384,372 | 5/1983 | Rector | 2/300 |
| 4,537,154 | 8/1985 | Kay | 119/857 |
| 5,201,446 | 4/1993 | Martin | 224/205 |
| 5,421,809 | 6/1995 | Rise | 602/19 |

Primary Examiner—Thomas Price

[57] ABSTRACT

To provide a harness device which has the effect of "settling" the heavy equipment driver's torso by counteracting the vibrational shock transmitted through muscle and fat masses in this area, thereby reducing soreness and fatigue. Said device consists of a two shoulder straps 2, which are traversed by chest strap 4, upper abdominal strap 6 in front and lower abdominal strap 8 in the front, and upper back strap 10 and lower back strap 12 at the rear (FIG. 1). Chest strap 4 has upper buckle 14 mounted at each terminal end which interconnect with the terminal ends of upper back strap 10. The terminal ends of upper abdominal strap 6 and lower abdominal strap 8 merge on each side and terminate with lower buckles 16, which interconnect to the terminal ends of lower back strap 12. The wearer lowers the harness over the head so that shoulder straps 2 rest over the shoulders; upper buckles 14 and the terminal ends of upper back straps 10 are connected together, and lower buckles 16 and the terminal ends of lower back strap 12 are connected together (FIG. 2).

2 Claims, 1 Drawing Sheet

5,671,699

TORSO-SETTLING HARNESS FOR TRUCK DRIVERS

BACKGROUND-FIELD OF INVENTION

This invention relates to harnesses and belts which are attached to the human body for comfort and support.

BACKGROUND-DESCRIPTION OF PRIOR ART

Many types of harnesses and belts have been devised to provide support to the human body during work. These designs range from lumbar support belts for workers who lift heavy objects (as disclosed by Carabelli et at.), to harnesses which ensure the safety of window washers or motorcycle passengers (as disclosed by Goldmacher). Although one of the most common complaints of long-distance truck drivers is fatigue and soreness caused by constant bouncing of a truck over poor roads, there are no prior art references which provide a remedy.

OBJECTS AND ADVANTAGES

Accordingly, I claim the following objects and advantages of my invention: a series of straps which from a body harness that not only braces a truck driver's back, but supports the abdomen, chest and rib cage as well. This has the effect of "settling" the driver's torso by counteracting the vibrational shock transmitted through muscle and fat masses in this area, thereby reducing soreness and fatigue. This device is useful not to long-distance truck's, but can be used by driver's/riders of off-road vehicles, construction equipment etc.

DRAWING FIGURES

DRAWING REFERENCE NUMERALS

2 Shoulder Strap(s)
4 Chest Strap
6 Upper Abdominal Strap
8 Lower Abdominal Strap
10 Upper Back Strap
12 Lower Back Strap
14 Upper Buckle
16 Lower Buckle
18 Torso

DESCRIPTION

Figure 1:
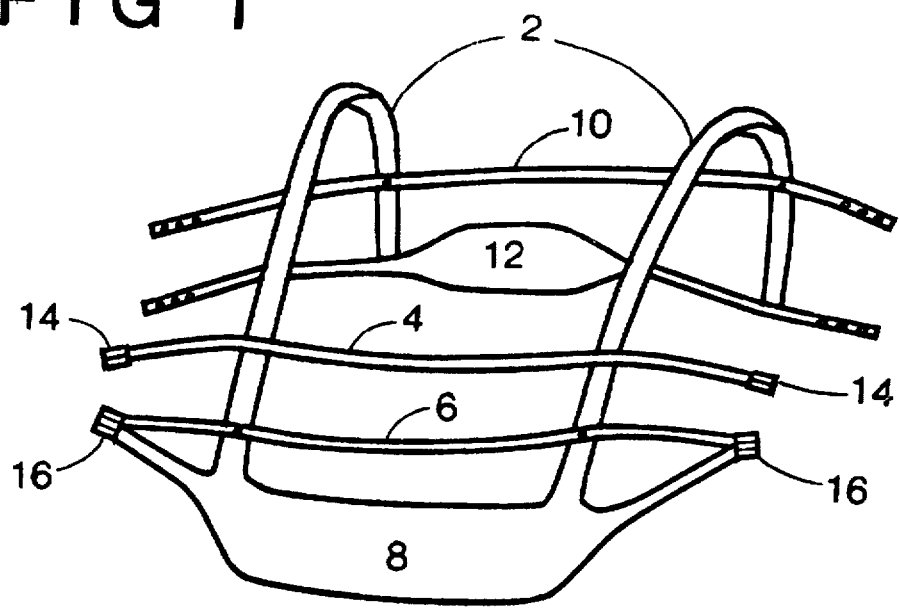
FIG. 1 shows a frontal/side view of the device.
Figure 2:
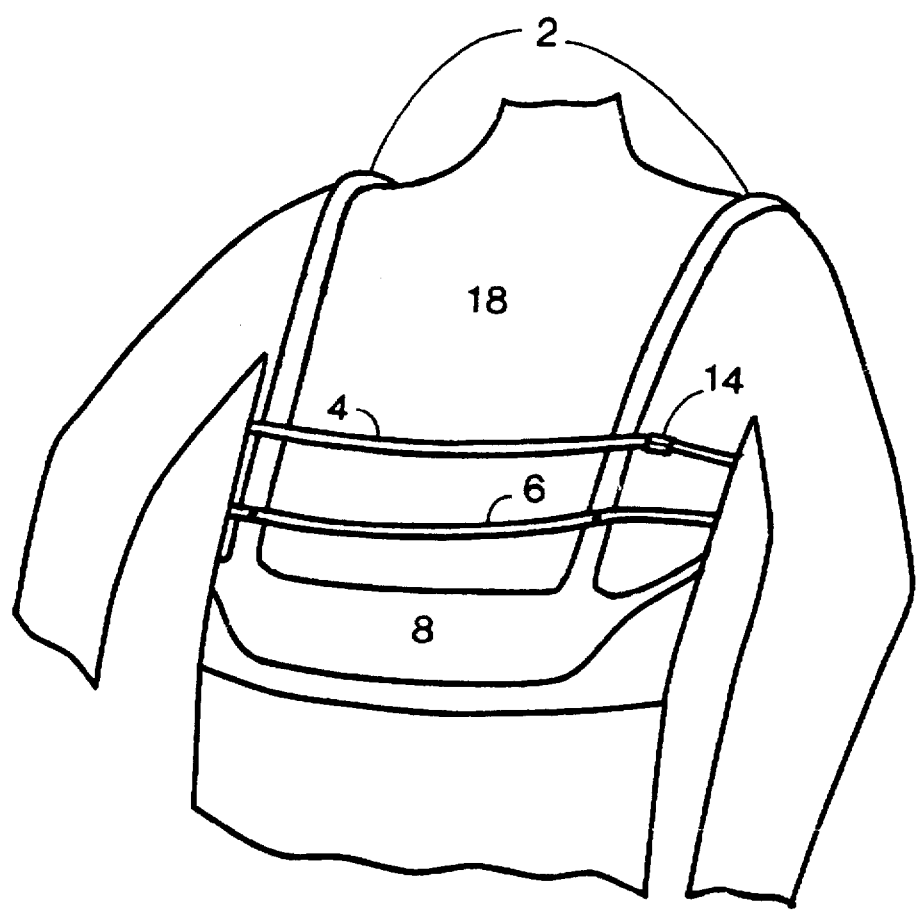
FIG. 2 shows a frontal/side view of the device as worn on the torso.

The preferred embodiment of this invention as shown in FIGS. 1 and 2 consists of the following. Two shoulder straps 2, which curve over the shoulders, are positioned in parallel relationship to each other and are of sufficient length to extend to the abdominal region at their anterior ends and to the lumbar region at their posterior ends. Said shoulder straps 2 terminate at their anterior ends in lower abdominal strap 8, which is positioned in perpendicular relationship to said shoulder straps. Lower abdominal strap 8 features a center section which is several times wider than its terminal ends; each of said ends has lower buckle 16 attached to it and is of sufficient length to allow said buckles to reach the sides of the torso 18. Upper Abdominal Strap 6 traverses shoulder straps 2 at mid-torso level in parallel relationship to lower abdominal strap 8 and chest strap 4. Terminal ends of upper abdominal strap 6 are of sufficient length to reach the sides of torso 18, where they are attached onto the terminal ends of lower abdominal strap 8 at or near lower buckles 16. Shoulder straps 2 terminate at their posterior ends in lower back strap 12, which is positioned in perpendicular relationship to said shoulder straps. Lower back strap 12 features a center section which is several times wider that its terminal ends; each of said ends features a plurality of holes which correspond to lower buckles 16, and has sufficient length to extend to the sides of the torso 18. Chest strap 4 traverses shoulder straps 2 at chest level in parallel relationship to lower abdominal strap 8. Terminal ends of strap 4 are of sufficient length to reach the sides of the torso 18, and terminate in upper buckles 14. Upper back strap 10 traverses the posterior sides of shoulder straps 2 at the upper back region of the torso, at a height which corresponds directly with height of chest strap 4. Said upper back strap 10 has terminal ends of sufficient length to reach the sides of the torso 18, and features plurality of holes which correspond with upper buckles 14. This entire harness is constructed of leather, cloth, vinyl or any other flexible, durable material.

OPERATION

In the preferred embodiment, the user applies their device by lowering it over the head, thereby allowing shoulder straps 2 to drape over the shoulders and lower abdominal strap 8 to face the front of the body. Each end of lower back strap 12 is inserted into its corresponding lower buckle 16, tightened and secured. Each end of upper back strap 10 is inserted into its corresponding upper buckle 14, tightened and secured. Tension of the buckles and straps should be set at a firmly supportive but comfortable level, with each strap resting across the area of the torso 18 for which it is named (FIG. 2).

Although the previous descriptions may present several specificities, these should not be construed by the reader as limitations of the invention's scope but as illustrations of the preferred embodiment thereof. Those skilled in the art may envision several other variations within this scope. The materials used to construct the straps can be any sufficiently flexible and durable material. Upper/lower buckles 14/16 can be substituted with velcro, snaps, hooks or a variety of adjustable fastening means. Moreover, the various straps which comprise the harness system can be attached together permanently, detachably or adjustably.

I claim:

1. A harness device consisting of a plurality of straps fabricated from a flexible and durable material, which is capable of reducing vibration-induced soreness of muscle and fat masses of the human torso, consisting of:

a) a main section which drapes across the human torso, comprising a pair of vertically-oriented shoulder strap members which are positioned in parallel relationship to each other, and are traversed at their anterior ends by a horizontally disposed abdominal strap member and traversed at their posterior end by a horizontally disposed lumbar strap member;

b) a pair of strap members mounted onto and in transverse relationship to the aforementioned shoulder straps, whereby one of said strap members forms a chest strap which is adjacent and parallel to the aforementioned abdominal strap and the other of said strap members forms an upper back strap which is positioned adjacent and parallel to the aforementioned lumbar strap member;

c) a horizontally disposed upper abdominal strap member, mounted onto the anterior side of shoulder straps and positioned between the chest and lower abdominal strap members so as to coincide with the upper abdominal region of the torso, said strap having terminal ends of sufficient length to extend around to the sides of the torso.

2. The harness device of claim 1, with the inclusion of:

a) terminal ends of the aforementioned chest and upper back strap members being sufficiently elongated to extend to the sides of the torso and be securely engaged together via an adjustable fastening means such as velcro, buckles or the like;

b) short end straps radiating from each side of and in the same horizontal plane as the aforementioned lower abdominal and lumber strap members being of sufficient length to extend to the sides of the torso and featuring adjustable fastening means so as to allow each side of said abdominal and lumbar strap members to be securely engaged together via said end straps;

c) terminal ends of the aforementioned upper abdominal strap member which on each side extend to and is mounted onto the lower abdominal strap member end straps positioned directly below.

* * * * *